United States Patent [19]

Reese

[11] Patent Number: 4,937,329

[45] Date of Patent: Jun. 26, 1990

[54] PRODUCTION OF 2,3'-ANHYDRO-2'-DEOXYURIDINE DERIVATIVES

[75] Inventor: Colin B. Reese, London, England

[73] Assignee: Efamol Holdings P.L.C., England

[21] Appl. No.: 269,752

[22] Filed: Nov. 8, 1988

[30] Foreign Application Priority Data

Nov. 13, 1987 [GB] United Kingdom ............... 8726585

[51] Int. Cl.$^5$ .......................................... C07H 17/00
[52] U.S. Cl. ..................................... 536/23; 544/95; 544/310
[58] Field of Search .................... 544/310, 95; 536/23

[56] References Cited

PUBLICATIONS

Dyatkina et al. Chem. Abst. 110-115237q (1989).
Veres et al. Chem. Abst. 110-91126z (1989).
El Kouni et al., Chem. Abst. 109-221912v (1988).
Hayauchi et al., Chem. Abst. 109-211404s (1988).
Sokolova et al. Chem. Abst. 108-38269f (1988).
Rideout et al. Chem. Abst. 107-52002z (1987).
Rideout et al. Chem. Abst. 107-40276d (1987).
Rideout et al. Chem. Abst. 106-38480b (1987).
Davies et al. Chem. Abst. 102-221138c (1985).
Davies et al. Chem. Abst. 101-192379d (1984).
Ajmera et al. Chem. Abst. 100-19719w (1984).
Buchanan et al., Chem. Abst. 90-138134m (1979).
Imazawa et al. Chem. Abst. 89-75431n (1978).
Shibuya et al., Chem. Abst. 88-121666x (1978).
MacCoss et al., Chem. Abst. 88-89968j (1978).
Ozaki, Chem. Abst. 86-5768s (1977).
Glinski, R. P., et al. J. Org. Chem., 38, 4299, (1973).
Michelson, A.M., and Todd, A. R., J. Chem. Soc., 816 (1955).
Fox, J. J. et al., J. Org. Chem., 28, 936 (1963).
Kowollik, E. et al., Tetrahedron Lett., 3863, (1969).
Gerrard, W., J. Chem. Soc., 218, (1940).
Yamazaki, Y., et al, Tetrahedron, 30, 1319, (1974).
Kim, S. et al., et al, Tetrahedron Lett., 27, 1925, (1986).
Staab, H. A. et al., Angew Chem., 73, 26, (1961).

Primary Examiner—Cecilia Shen

Attorney, Agent, or Firm—Lowe, Price, LeBlanc, Becker & Shur

[57] ABSTRACT

A process for the production of a 5-substituted derivative of a 2,3'-anhydro-2'-deoxyuridine preferably corresponding to the following general formula:

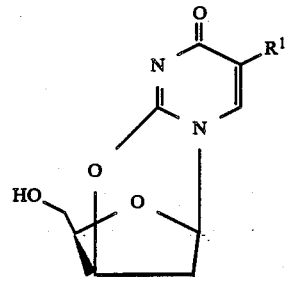

wherein $R^1$ represents H, alkyl, aryl, halogeno or $CF_3$; characterized in that it comprises heating a 5-substituted derivative of a 2'-deoxyuridine preferably corresponding to the following general formula:

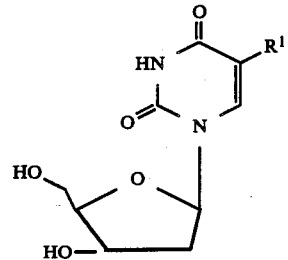

wherein $R^1$ is as defined above; in the presence of a sulphite transfer reagent and preferably a solvent is disclosed.

This process improves the production of valuable intermediates and hence facilitates and reduces the cost of production of pharmacologically-interesting compounds.

8 Claims, No Drawings

PRODUCTION OF 2,3'-ANHYDRO-2'-DEOXYURIDINE DERIVATIVES

This invention relates to the production of 2,3'-anhydro-2'-deoxyuridine derivatives; more particularly, it relates to an improved process for the production of a 5-substituted derivative of a 2,3'-anhydro-2'-deoxyuridine, such as 2,3'- anhydrothymidine, which may be used as an intermediate in the production of 3'-azido-3'-deoxythymidine (AZT), for example.

The anti-AIDS drug, AZT:

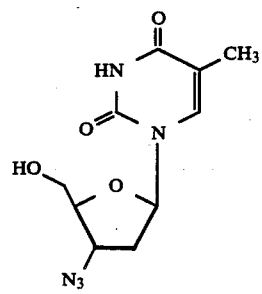

may readily be prepared in one step by the action of azide ions, e.g. lithium azide, on 2,3'-anhydrothymidine:

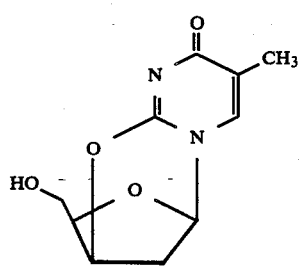

(see, for example, Glinski, R. P., et al. J. Org. Chem., 38, 4299, (1973)).

The original preparations of the latter compound involve the use of protecting groups and are cumbersome (see, for example, Michelson. A. M., and Todd, A. R., J. Chem. Soc., 816, (1955); Fox. J. J., and Miller, N. C., J. Org. Chem., 28, 936, (1963)).

An effectively one step conversion of thymidine:

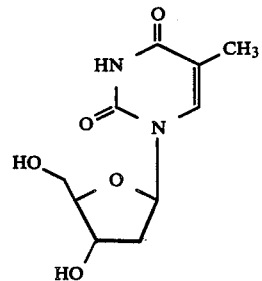

to 2,3'-anhydrothymidine, which involves the use of 1-chloro-1,2,2trifluoro-2-diethylaminoethane, has been reported (see, for example, Kowollik, E., et al, Tetrahedron Lett., 3863, (1969)). However, by this means the isolated yield of 2,3'-anhydrothymidine was only 40%, even when the reaction was carried out on a large scale (starting with 55 g of thymidine), (see, for example, Glinski et al, loc cit).

The present invention relates to an improved process for the production of 2,3'-anhydro-2'-deoxyuridine derivatives. By way of illustration of this advantageous process, it allows 2,3'-anhydrothymidine to be obtained from thymidine in one step in yields of almost 65%. Such compounds are, inter alia valuable intermediates for the production of AZT and related deoxynucleoside derivatives by known means and the application of the present process reduces the overall cost.

The present invention provides a process for the production of a 5-substituted derivative of a 2,3'-anhydro-2'-deoxyuridine characterised in that it comprises heating a corresponding 5-substituted derivative of a 2'-deoxyuridine in the presence of a sulphite transfer reagent.

More particularly, the present invention provides a process for the production of a 5-substituted derivative of a 2,3'-anhydro 2'-deoxyuridine corresponding to the following general formula:

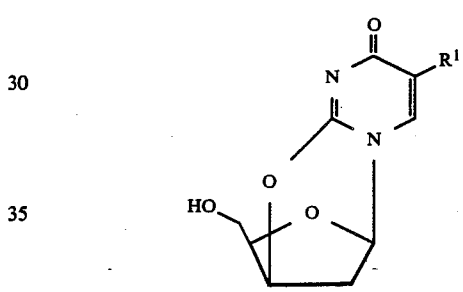

wherein $R^1$ represents H, alkyl, for example $C_1$-$C_6$ alkyl, in particular $CH_3$, aryl, halogeno, for example fluoro or iodo, or $CF_3$; characterised in that it comprises heating a 5-substituted derivative of a 2'-deoxyuridine corresponding to the following general formula:

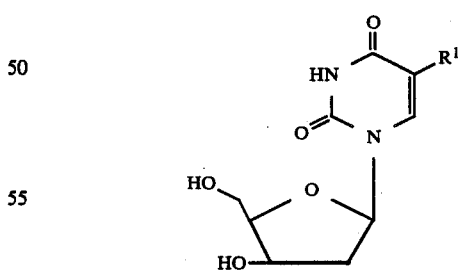

wherein $R^1$ is as defined above; in the presence of a sulphite transfer reagent, such as a diaryl sulphite, and a solvent, in particular a polar nonhydroxylic organic solvent. Generally, a catalyst is also used.

In general terms, the present process utilises a sulphite transfer reagent, such as diphenyl sulphite, to generate putative intermediate nucleoside 3',5'-cyclic sulphites, such as:

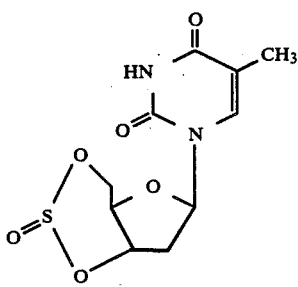

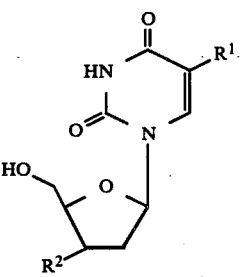

which decompose on heating to give anhydronucleosides, such as 2,3'-anhydrothymidine.

For example, when thymidine is heated at ca 156° C. for 45 minutes with a four fold excess of diphenyl sulphite (see, for example, Gerrard, W., J. Chem. Soc., 218, (1940)) in the presence of a catalytic amount of N-methylimidazole in N,N-dimethylacetamide solution, and is then worked-up under basic conditions. 2,3'-anhydrothymidine may easily be isolated in almost 65% yield.

In the above exemplified process, N,N-dimethylacetamide may be replaced by, for example, N,N-dimethylformamide or hexamethylphosphoric triamide (HMPA) Other catalysts, such as sodium hydrogen carbonate, may also be used.

The present invention is not limited as regards the sulphite transfer reagent. For example, thionyl chloride ($SOCl_2$) or di (4-chlorophenyl) sulphite (see, for example, Yamazaki, Y., et al, Tetrahedron, 30, 1319, (1974)):

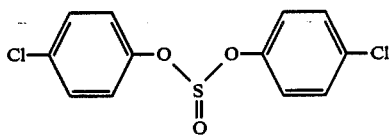

or di-(2-pyridyl) sulphite:

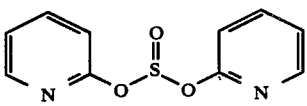

(see, for example, Kim, S., and Yi, K. Y., Tetrahedron Letr., 27, 1925, (1986));
or a 1,1'-sulphinyldi-imidazole:

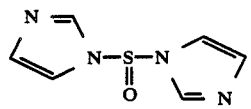

(see, for example, Staab, H. A., and Wendel, K., Angew. Chem., 73, 26, (1961)), are potentially more reactive sulphite transfer reagents.

A preferred use for compounds produced in accordance with the present invention is as intermediates in the production of AZT and related deoxynucleoside derivatives, for example, corresponding to the following general formula:

wherein $R^1$ is as defined above; and, in addition to $N_3$, $R^2$ may represent F, S-aryl (and hence $SO_2$-aryl, the corresponding sulphones, and H, the corresponding 2',3'-dideoxynucleosides), S-alkyl (and hence $SO_2$-alkyl, the corresponding sulphones), SCN and SeCN. In a preferred embodiment of the present process, thymidine ($R^1$ represents $CH_3$) may be transformed to 2,3'-anhydro thymidine, which may then be converted to AZT ($R^1$ represents $CH_3$; $R^2$ represents $N_3$), for example, by known means.

The following further illustrates the present invention:

Preparation of 2,3'-anhydrothymidine

A flask containing a stirred mixture of thymidine (5.0 g, 20.6 mmol), diphenyl sulphite (19.34 g, 82.6 mmol), N-methylimidazole (0.34 ml. 4.27 mmol) and N,N-dimethylacetamide (50 ml) was immersed in an oil bath, maintained at 156°±1° C. After 45 minutes, the products were cooled to 0° C. and were then poured, with stirring, into a cooled (0°C.) mixture of triethylamine (50 ml) and water (90 ml). After 40 minutes, by which time it had warmed up almost to room temperature, the resulting solution was extracted with chloroform (4×50 ml). The remaining aqueous layer was concentrated under reduced pressure and the viscous oil obtained was dissolved in absolute ethanol (30 ml), and the solution was re-evaporated. After one further evaporation from absolute ethanol (30 ml) solution, the residue was triturated with ether (3×30 ml). Dichloromethane (50 ml) was then added and the resulting colourless solid precipitate was collected by filtration and washed with dichloromethane (2×10 ml). After the combined filtrate and washings had been concentrated to ca. 30 ml, petroleum ether (b.p. 30°–40° C. 15 ml) was added, and the resulting mixture was refrigerated (4° C.) for 24 hr. A second crop of colourless solid was obtained; it was collected by filtration and was washed with dichloromethane (2×5 ml). The two crops of colourless solid were combined and dried in vacuo at 75° C. to give virtually pure 2,3'-anhydrothymidine [found, in material recrystallized from 90% ethanol and dried in vacuo over $P_2O_5$ at 100° C.: C,49.6; H,5.7; N,11.6. $C_{10}H_{12}N_2O_4$. $H_2O$ requires: C,49.6; H,5.8; N,11.6%]; yield, 3.0 g (64.8%); $R_F$ 0.38 [butan-1-ol - acetic acid - water (5:2:3 v/v]; $\lambda_{max}$ (95% ethanol): 247.5 ($\epsilon$7 760), $\lambda_{min}$ 219 nm ($\epsilon$4 750); $\delta_H$ [$d_6$-DMSO, 250 MHz]: 1.76(3H,d, J 0.9 Hz), 2.4–2.6 (2H,m), 3.49 (2H,m), 4.19(1H, dt, J 2.4, 6.5 Hz), 5.04 (1H,t, 5.4 Hz), 5.25(1H,m), 5.82 (1H,d, 3.7 Hz , 7.56 (1H,m).

Conversion to 3'-azido-3'-deoxythymidine 2,3'-Anhydrothymidine (0.673 g, 3.0 mmol), lithium azide (0.4 g, 9.0 mmol) and N,N-dimethylacetamide (7.5 ml) were heated together with stirring at 130° C. for 16 hr. The products were then worked-up and chromatographed on silica gel to give 3'-azido-3'-deoxythymidine (0.64 g, 80%). identical to authentic material.

I claim:

1. A process for the production of a 5-substituted derivative of a 2,3'-anhydro-2'-deoxyuridine which comprises heating a corresponding 5-substituted derivative of a 2'-deoxyuridine in the presence of a sulphite transfer reagent at a sufficient temperature and for a time to produce said 2,3'-anhydro-2'-deoxyuridine.

2. A process as claimed in claim I wherein the 5-substituted derivative of 2,3'-anhydro-2'-deoxyuridine corresponds to the following formula:

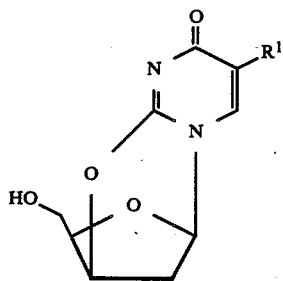

wherein $R^1$ represents H, alkyl, aryl, halogeno or $CF_3$; and the 5-substituted derivative of a 2'-deoxyuridine corresponds to the following formula:

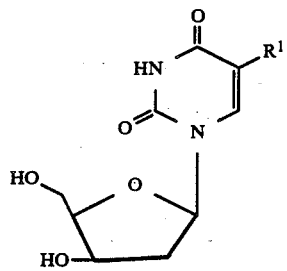

wherein $R^1$ is as defined above; and wherein the heating is carried out in the presence of a sulphite transfer reagent and in the presence of a solvent.

3. A process as claimed in claim 1 or claim 2 wherein the sulphite transfer reagent is selected from thionyl chloride, diphenyl sulphite, di-(4-chlorophenyl) sulphite, di-(2-pyridyl) sulphite and 1,1'-sulphinyldi imidazole.

4. A process as claimed in claim 2 wherein $R^1$ represents $CH_3$.

5. A process as claimed in any one of claims 2 to 4 wherein a polar non-hydroxylic organic solvent is used.

6. A process as claimed in any one of claims 2 to 5 wherein the solvent is selected from N,N dimethylacetamide. N,N-dimethylformamide or hexamethylphosphoric triamide.

7. A process as claimed in any one of claims 1 to 6 wherein a catalyst is used.

8. A process as claimed in claim 7 wherein the catalyst is N-methylimidazole or sodium hydrogen carbonate.

* * * * *